United States Patent [19]

Goegelman et al.

[11] 4,399,274

[45] Aug. 16, 1983

[54] ISOLATION OF NON-IONIC LIPOPHILIC MATERIALS ON MACRORETICULAR POLYMERIC ABSORBENTS

[75] Inventors: Robert T. Goegelman, Linden; Laszlo R. Treiber, Gillette, both of N.J.

[73] Assignee: Merck & Co., Inc., Rahway, N.J.

[21] Appl. No.: 279,633

[22] Filed: Jul. 2, 1981

[51] Int. Cl.$^3$ .............................................. C07H 17/08
[52] U.S. Cl. .................................... 536/7.1; 210/674; 210/692
[58] Field of Search ............... 210/671, 674, 690, 692, 210/693, 908–910; 435/119, 886; 536/17 R, 7.1

[56] References Cited

U.S. PATENT DOCUMENTS

| | | | |
|---|---|---|---|
| 2,974,178 | 3/1961 | Hwa et al. | 210/690 |
| 3,531,463 | 9/1970 | Gustafson | 210/674 |
| 4,042,498 | 8/1977 | Kennedy | 210/674 |
| 4,160,083 | 7/1979 | Cole | 536/7.1 |
| 4,160,084 | 7/1979 | Miller et al. | 536/7.1 |
| 4,160,861 | 7/1979 | Cole et al. | 536/7.1 |
| 4,161,583 | 7/1979 | Wilson et al. | 536/7.1 |
| 4,171,314 | 10/1979 | Chabala et al. | 536/7.1 |
| 4,172,940 | 10/1979 | Chaiet | 536/7.1 |
| 4,173,571 | 11/1979 | Chabala et al. | 536/7.1 |
| 4,199,569 | 4/1980 | Chabala et al. | 536/7.1 |
| 4,200,581 | 4/1980 | Fisher et al. | 536/7.1 |
| 4,201,861 | 5/1980 | Mrozik et al. | 536/7.1 |
| 4,206,205 | 6/1980 | Mrozik et al. | 536/7.1 |

FOREIGN PATENT DOCUMENTS 1573955 8/1980 United Kingdom .

*Primary Examiner*—Ivars C. Cintins
*Attorney, Agent, or Firm*—David L. Rose; Mario A. Monaco

[57] ABSTRACT

Non-ionic, lipophilic substances are isolated from aqueous or aqueous-organic solution by treatment with a macroreticular polymeric absorbent followed by elution with additional or a different organic solvent.

1 Claim, No Drawings

ISOLATION OF NON-IONIC LIPOPHILIC MATERIALS ON MACRORETICULAR POLYMERIC ABSORBENTS

BACKGROUND OF THE INVENTION

This invention is concerned with a process for isolating non-ionic lipophilic substances from solution in water, organic solvents or miscible mixtures thereof which comprises treating the solution with an insoluble, synthetic resin which is an addition copolymer having a cross-linked structure and which optionally has been pre-treated with an organic solvent.

It is well known to use ion-exchange resins to selectively absorb certain ionically charged substances from aqueous systems, the absorption being the result of ionic forces. It is also known that insoluble synthetic resins of the type used in the present invention can effectively be employed to concentrate or separate organic solvents from aqueous mixtures thereof (U.S. Pat. No. 2,974,178) such as in the delivery of potable water from source water contaminated with traces of organic solvents.

Now, with the present invention, there is provided a method of concentrating or separating non-ionic lipophilic substances from solutions in water, organic solvents or miscible mixtures thereof which comprises treating the solution with an insoluble, synthetic resin which is an addition copolymer having a cross-linked structure followed by elution of the resin with an organic solvent.

The novel method is comparable in some respects to liquid-liquid extraction combining the benefits of a counter-current system, but one in which the "organic phase" is stationary and one in which there are no interfacial emulsions. Subsequent elution of the solvent-impregnated resin with an appropriate solvent or sequence of solvents permits recovery of the non-ionic lipophilic substances and separation thereof in situations where a multiplicity of such substances are present.

DETAILED DESCRIPTION OF THE INVENTION

This invention is concerned with a novel process for isolating and separating non-ionic, lipophilic substances from solution in water, organic solvents or miscible mixtures thereof which comprises treating the solution with an insoluble synthetic resin which is an addition copolymer having a cross-linked structure and which optionally has been pretreated with an organic solvent, followed by elution of the resin with an organic solvent or sequence of organic solvents.

The insoluble synthetic organic resins useful in the novel process of this invention are those generally known as macroreticular polymeric absorbents and are of the type described in *Industrial and Engineering Chemistry, Product Research and Development,* 12, 56 (1973). They include the Amberlite ® XAD group of resins from Rohm and Haas Co., Philadelphia, Pa; the Duolite ES group of resins from Chemical Process Co., Redwood City, Calif; and DIAION ® HP Series of resins from Mitsubishi Chemical Industries Limited, Tokyo, Japan.

The miscible aqueous organic solvent mixtures of the novel process are composed of water and one or more inert organic solvent(s) in at least one of which the substance to be isolated is soluble, and in such proportions that the components of the mixture are miscible at the temperature of the process. Contemplated within the scope of the invention are mixtures wherein the components are completely miscible in all proportions such as methanol and water, or acetone and water, as well as mixtures wherein the components have only very limited miscibility, such as toluene and water.

The macroreticular polymeric adsorbents useful in this invention are hydrophobic and have the ability to absorb and retain organic solvents, swelling in the process. If one of these resins is pretreated with an organic solvent, separated from excess solvent and then treated with a solution of a lipophilic solute, the solute suffers partition between the original solvent and the organic solvent phase absorbed in the resin. The extent of the partition depends on the solubility characteristics of the solute, and the residence time. After separation of the excess solvent from the resin the absorbed organic solvent solution of the solute can be eluted from the resin with additional organic solvent.

In another aspect of the present invention, if the desired solute or solutes to be isolated are present in a miscible aqueous organic solvent mixture, the mixture can be treated with one of the resins useful in this invention with or without pre-treatment with a solvent in which case the hydrophobic nature of the resin permits absorption of organic solvent solution of the lipophilic solute with the exclusion of water. Following separation of excess non-absorbed liquid from the resin, the lipophilic solute or solutes may be eluted from the resin with additional organic solvent.

The novel process of this invention has the advantage of very easy operation. It may be conducted as a batch process in which losse resin is mixed with the solutions and ultimately separated by filtration, centrifugation, decantation or the like. Alternatively, it can be conducted with the resin in a column through which the solutions are percolated.

Overall, the novel process is essentially a partition of a lipophilic solute between two solvent systems. There results a concentration of solute relative to the volume of solvent. There also results a separation of lipophilic solute from any hydrophilic solutes. And very importantly the liquid-liquid extraction is conducted without the formation of emulsions which are so often troublesome and wasteful of time and materials.

The novel process of this invention is particularly useful in the isolation of fermentation products. These materials are often non-ionic, lipophilic solutes in very dilute aqueous solution accompanied by numerous ionic materials such as pH control agents and nutrients. Much of it may also be intracellular material and readily removed from the mycelia by adding an organic solvent to the whole broth. Frequently, the mycelia are first separated from the broth and then extracted with solvent or solvent mixtures to remove intracellular material. Such extracts also lend themselves to use in the novel process of this invention. The present invention provides an excellent method of isolating the non-ionic, lipophilic fermentation product from the resulting solvent-water mixture.

The following examples illustrate the utility of the novel process of the present invention with reference to the isolation of avermectin from fermentation broths and separation of its components. The examples are illustrative only and are not intended to be restrictive of the scope of the invention.

The avermectin fermentation broths used in the following examples are produced by the organisms, media, and methods described in British Pat. No. 1,573,955.

The microorganisms capable of producing avermectins are of a new species of the genus Streptomyces, which has been named *Streptomyces avermitilis*. One such culture, isolated from soil, is designated MA-4680 in the culture collection of Merck & Co. Inc., Rahway, New Jersey. A sample of this culture has been deposited in the permanent culture collection of the Fermentation Section of the Northern Utilization Research Branch, U.S. Department of Agriculture at Peoria, Illinois, and has been assigned the accession number NRRL 8165. A sample of NRRL 8165 has also been deposited, without restriction as to availability, in the permanent culture collection of the American Type Culture Collection at 12301 Parklawn Drive, Rockville, Maryland 20852, and has been assigned the accession number ATCC 31,267.

A strain of *Streptomyces avermitilis*, MA 4848, was isolated after irradiation with ultraviolet light of *Streptomyces avermitilis* MA 4680. A lyophilized tube and a frozen vial of this culture have been deposited in the permanent culture collection of the American Type Culture Collection, and they have been assigned the accession numbers 31272 and 31271 respectively. Slightly higher fermentation yields of C-076 have been obtained using this frozen stock as inoculum.

A typical fermentation is as follows:

A 250 ml baffled Erlenmeyer flask containing 50 ml of the following medium:

| Lactose | 2.0% |
|---|---|
| Distiller's solubles | 1.5% |
| Autolysed yeast, Ardamine pH | 0.5% |
| pH - before sterilization | 7.0 | is inoculated with the contents of one frozen vial of *Streptomyces avermitilis* MA 4848 and incubated on a rotary shaker at 28° C. for 24 hours at 150 RPM.

The above fermentation medium (10 ml) is used to inoculate 500 ml of the same medium as above in a 2 liter baffled Erlenmeyer flask. The fermentation medium is incubated at 150 RPM on a rotary shaker at 28° C. for 24 hours.

All of the foregoing medium is used to inoculate 467 liters of the following medium in a 756 liter stainless steel fermentor:

| Lactose | 2.0% |
|---|---|
| Distiller's solubles | 1.5% |
| Autolysed yeast, Ardamine pH | 0.5% |
| Polyglycol 2000 | 0.32 ml/liter |
| pH - before sterilization | 7.0 |

The fermentation medium is incubated at 28° C. for 40 hours with an air flow of 10 cubic feet per minute and an agitation rate of 130 RPM.

The above medium (230 L) is used to inoculate 4310 liters of the following medium in a 5670 liter stainless steel fermentor:

| Dextrose | 4.5% |
|---|---|
| Peptonized milk | 2.4% |
| Autolysed yeast, Ardamine pH | 0.25% |
| Polyglycol 2000 | 2.5 ml/liter |
| pH - before sterilization | 7.0 |

The fermentation continues for 144 hours at 26° C. with an air flow rate of 54.3 cubic feet per minute and agitation of 120 RPM.

The avermectin series of compounds have the following structure:

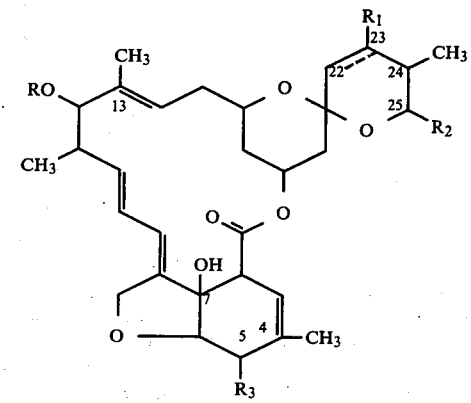

wherein R is the 4'-(α-L-oleandrosyl)-α-L-oleandrose group of the structure:

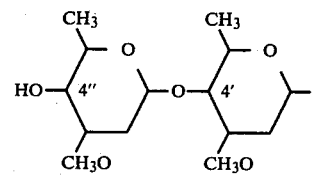

and wherein the broken line indicates a single or a double bond;

$R_1$ is hydroxy and is present only when said broken line indicates a single bond;

$R_2$ is iso-propyl or sec-butyl; and $R_3$ is methoxy or hydroxy.

There are eight major C-076 compounds and they are given the designations A1a, A1b, A2a, A2b, B1a, B1b, B2a, B2b based upon the structure of the individual compounds.

In the foregoing structural formula, the individual C-076 compounds are as set forth below.

| | $R_1$ | $R_2$ | $R_3$ |
|---|---|---|---|
| A1a | Double bond | sec-butyl | —OCH$_3$ |
| A1b | Double bond | iso-propyl | —OCH$_3$ |
| A2a | —OH | sec-butyl | —OCH$_3$ |
| A2b | —OH | iso-propyl | —OCH$_3$ |
| B1a | Double bond | sec-butyl | —OH |
| B1b | Double bond | iso-propyl | —OH |
| B2a | —OH | sec-butyl | —OH |
| B2b | —OH | iso-propyl | —OH |

EXAMPLE 1

Resin Treatment of Aqueous-Methanol Mycelial Extract

Whole broth (1 l) was mixed with 50 g of diatomaceous earth and filtered. The filter cake was washed with water, then suspended in 400 ml of 55% (by volume) aqueous methanol. The suspension was slowly filtered and the filter cake was washed with 600 ml more of 55% (by volume) aqueous methanol. The combined extracts (980 ml) were fed directly to a column of Amberlite ® XAD-2 resin (20–50 mesh, 63 ml, 38 cm high) at a flow rate of 4 ml/min. The percolate showed no signs (TLC) of breakthrough of avermectin during the entire loading procedure.

The column was washed with 200 ml of water and then eluted with methanol at a flow rate of 4 ml/min. Nine fractions of approximately 10 ml and one of 5 ml were collected. The results are shown in Table I.

TABLE I

| Sample | | Vol. (ml) | B1a Conc. (μg/ml) | B1a Total (mg) | B1a Yield (%) | C076 Conc. (μg/ml) | C076 Total (mg) | C076 Yield (%) | Solids (mg/ml) | Purity (%) B1a | Purity (%) C076 |
|---|---|---|---|---|---|---|---|---|---|---|---|
| Feed | | 980 | 101 | 99.0 | 100 | 384 | 376 | 100 | 1.30 | 7.79 | 34.0 |
| Spt. | 1. | 720 | — | — | — | — | — | — | 0.37 | — | — |
| | 2. | 260 | — | — | — | — | — | — | 0.36 | — | — |
| Wash | | 200 | — | — | — | — | — | — | — | — | — |
| Fr. | 1. | 10.3 | 1234 | 12.7 | 12.8 | 4348 | 44.8 | 11.9 | 8.24 | 15.0 | 52.8 |
| | 2. | 10.7 | 567 | 6.07 | 6.13 | 2124 | 22.7 | 6.04 | 7.74 | 7.33 | 27.4 |
| | 3. | 10.5 | 2903 | 30.5 | 30.8 | 10715 | 112.5 | 29.9 | 22.8 | 12.7 | 47.0 |
| | 4. | 10.0 | 2711 | 27.1 | 27.4 | 9772 | 97.7 | 26.0 | 16.1 | 16.8 | 60.6 |
| | 5. | 9.7 | 1297 | 12.6 | 12.7 | 4784 | 46.4 | 12.3 | 8.81 | 14.7 | 54.3 |
| | 6. | 10.2 | 623 | 6.35 | 6.42 | 2426 | 24.7 | 6.58 | 5.23 | 11.9 | 46.4 |
| | 7. | 10.2 | 251 | 2.56 | 2.59 | 1019 | 10.4 | 2.76 | 3.13 | 8.03 | 32.6 |
| | 8. | 10.5 | 47.8 | 0.50 | 0.51 | 218 | 2.29 | 0.61 | 1.97 | 2.43 | 11.1 |
| | 9. | 10.0 | 46.6 | 0.47 | 0.47 | 281 | 2.81 | 0.75 | 1.26 | 3.69 | 22.3 |
| | 10. | 5.0 | 20.0 | 0.10 | 0.10 | 140 | 0.70 | 0.19 | n.a. | n.a. | n.a. |
| Comb 1-7 | | 71.6 | 1367 | 98.9 | 98.9 | 5017 | 359 | 95.5 | 10.3 | 13.3 | 48.7 |

: not assayed

EXAMPLE 2

Resin Treatment of Aqueous Methanol Mycelial Extract and Isolation of Avermectin Using the procedure substantially as described in Example 1 with the following details, the results described in Table II were obtained:
Whole Broth: 1920 ml
Extract Volume: 1900 ml
Resin: Amberlite ® XAD-2, 20–50 mesh, 25 ml, 31 cm high
Feed: 810 ml at 1.7 ml/min. Feed was stopped when breakthrough ocurred.
Wash: 55% (by vol) aqueous methanol
Elution: methanol at 1.7 ml/min.

Fractions 4–8 were pooled to give 25 ml of a composite sample and evaporated to dryness. The residue was dissolved in 5 ml of toluene and separated from a slight insoluble residue. Dilution with 5 ml of petroleum ether caused crystallization. The crystals were isolated by centrifugation and decantation and were washed twice with 5 ml of petroleum ether-toluene (1:1 by vol) solution.

TABLE II

| Sample | | Vol. (ml) | B1a Conc. (μg/ml) | B1a Total (mg) | B1a Yield (%) | C076 Conc. (μg/ml) | C076 Total (mg) | C076 Yield (%) | Solids (mg/ml) | Purity (%) B1a | Purity (%) C076 |
|---|---|---|---|---|---|---|---|---|---|---|---|
| Feed | | 810 | 113.7 | 92.1 | 100 | 444 | 360 | 100 | 1.11 | 10.2 | 39.9 |
| Stp. | 1–35. | 700 | 2.35 | 1.65 | 1.79 | 8.26 | 5.8 | 1.61 | 0.37 | 0.63 | 2.21 |
| | 36–41. | 120 | 8.03 | 0.96 | 1.05 | 33.9 | 4.1 | 1.13 | 0.41 | 1.95 | 8.23 |
| Wash | 42. | 20 | 45.1 | 0.90 | 0.98 | 192 | 3.8 | 1.07 | 0.61 | 7.37 | 31.4 |
| | 43. | 20 | 63.1 | 1.26 | 1.37 | 253 | 5.1 | 1.40 | 0.54 | 11.6 | 46.7 |
| FR | 1–3. | 15 | 58.5 | 0.88 | 0.95 | 230 | 3.5 | 0.96 | 0.58 | 10.1 | 39.5 |
| | 4. | 5 | 3780 | 18.9 | 20.5 | 13202 | 66.0 | 18.4 | 25.6 | 14.8 | 51.7 |
| | 5. | 5 | 4816 | 24.1 | 26.2 | 16721 | 83.6 | 23.3 | 35.2 | 13.7 | 47.5 |
| | 6. | 5 | 3034 | 15.2 | 16.5 | 11012 | 55.1 | 15.3 | 23.6 | 12.9 | 46.6 |
| | 7. | 5 | 1677 | 8.39 | 9.10 | 6131 | 30.7 | 8.52 | 14.4 | 11.7 | 42.7 |
| | 8. | 5 | 997 | 4.99 | 5.41 | 3672 | 18.4 | 5.11 | 9.67 | 10.3 | 38.0 |
| | 9. | 5 | 591 | 2.96 | 3.21 | 2355 | 11.8 | 3.27 | 6.06 | 9.75 | 38.9 |
| | 10. | 5 | 379 | 1.90 | 2.06 | 1255 | 6.3 | 1.74 | 4.11 | 9.22 | 30.5 |
| | 11. | 5 | 240 | 1.20 | 1.30 | 997 | 5.0 | 1.39 | 2.85 | 8.42 | 35.0 |
| | 12. | 5 | 150 | 0.75 | 0.81 | 634 | 3.2 | 0.88 | 2.15 | 6.98 | 29.5 |
| | 13. | 5 | 88.8 | 0.44 | 0.48 | 373 | 1.9 | 0.52 | 1.53 | 5.80 | 24.4 |
| Comp. | 4–8. | 25 | 2863 | 71.6 | 77.7 | 10152 | 254 | 70.5 | 21.7 | 13.2 | 46.8 |

The crystals were shown to consist of: B1a, 19.4 mg (purity 28.9%). Yield 33.9% C076, 42.9 mg (purity 63.8%). Yield 21.1%

EXAMPLE 3

Utility of Duolite ® ES-863 Resin

The starting material was a mycelial extract in 60% (by volume) aqueous acetone and had the component concentrations shown as determined by HPLC.

| Component | Conc. (mg/ml.) |
|---|---|
| B2b | 30 |
| B2a | 460 |
| A2b | 71 |
| B1b | 103 |
| A2a | 361 |
| B1a | 629 |
| A1b | 94 |
| A1a | 229 |
| TOTAL | 1976 |

A series of acetone-water mixtures was prepared as shown below by adding water to 5 ml aliquots of the above solution. The samples were centrifuged and the supernatants were assayed.

| Sample | Water (ml) | % Acetone (vol) |
|---|---|---|
| 1 | 0 | 60.0 |
| 2 | 1.0 | 50.0 |
| 3 | 2.0 | 42.9 |
| 4 | 3.0 | 37.5 |
| 5 | 4.0 | 33.3 |
| 6 | 5.0 | 30.0 |
| 7 | 6.0 | 27.3 |
| 8 | 7.0 | 25.0 |
| 9 | 8.0 | 23.1 |
| 10 | 9.0 | 21.4 |

After standing overnight they were centrifuged and 4 ml of each supernatant was transferred to tubes containing 1 g each of purified ES-863 resin. An aliquot was also taken for HPLC assay.

The samples containing the resin were equilibrated for an hour, then centrifuged. The supernatants were assayed by HPLC. A comparison of the assays before and after equilibration represent the partition between the solvent and the adsorbent. Table III shows the material remaining in solution as a percentage of the starting concentration as a function of acetone concentration.

By similar procedures, mixtures with higher acetone concentrations were also tested and the combined results are included in Table III.

The resin employed in the foregoing was purified as follows:
(1) exhaustive acetone wash;
(2) exhaustive toluene wash;
(3) acetone wash;
(4) water wash;
(5) drying at 110° C.

TABLE III

| | % Remaining in Solution | | | | | | | | |
|---|---|---|---|---|---|---|---|---|---|
| Acetone % | B2b | B2a | A2b | B1b | A2a | B1a | A1b | A1a | C076 |
| 60.0 | 33.3 | 4.95 | 0.3 | 1.53 | 2.72 | 3.17 | 1.69 | 2.10 | 3.51 |
| 50.0 | 4.35 | 1.36 | 0.57 | 0.90 | 2.12 | 2.28 | 2.42 | 3.03 | 2.01 |
| 42.9 | 3.89 | 2.65 | 1.71 | 2.13 | 3.76 | 3.71 | 3.13 | 4.39 | 3.32 |
| 37.5 | <3 | 3.21 | 2.70 | 2.59 | 4.19 | 3.85 | 3.18 | 3.60 | 3.50 |
| 33.3 | 1.29 | 4.37 | 2.57 | 3.73 | 6.23 | 6.41 | 5.35 | 7.82 | 5.67 |
| 27.3 | 2.34 | 5.37 | 3.73 | 4.55 | 6.99 | 6.81 | 6.42 | 8.42 | 6.36 |
| 25.0 | 5.08 | 7.29 | 5.38 | 6.32 | 7.86 | 7.72 | 5.63 | 7.09 | 7.36 |
| 23.1 | 4.80 | 6.09 | 3.89 | 5.03 | 6.54 | 6.86 | 4.85 | 6.75 | 6.29 |
| 21.4 | <2 | 5.10 | 2.75 | 3.73 | 5.36 | 5.41 | 4.56 | 4.40 | 4.84 |
| 68.0 | | 27.8 | 26.8 | 20.4 | 15.2 | 14.3 | 10.6 | 5.68 | 20.2 |
| 73.3 | | 60.4 | 64.8 | 5.15 | 42.1 | 39.4 | 68.1 | 19.7 | 51.0 |
| 77.1 | | 82.1 | 94.4 | 73.8 | 65.7 | 60.4 | 111 | 36.2 | 76.0 |
| 80.0 | | 99.8 | 117 | 94.2 | 86.7 | 78.4 | 145 | 51.5 | 96.3 |
| 82.2 | 135 | 165 | 128 | 123 | 110 | 199 | 79.0 | 136 | |

The % numbers greater than 100 indicate that the resin was swollen, but C076's were not absorbed. As solvent was removed by the resin, the liquid phase became more concentrated.

EXAMPLE 4

Use of Duolite® ES-863 Resin

Resin Column: Duolite ES-863 resin, 26 cm, 21 ml equilibrated with 50% (by vol) aqueous acetone.
Feed Solution: The mycelial extract of Example 3 was treated with sufficient water to change it to 50% (by vol) aqueous acetone. Then 60 ml of 50% aqueous acetone was added to 600 ml of the solution in order to redissolve precipitate. 200 ml was used.
Gradient Elution:
Flow rate: 1.00 ml/min.
Water: 5 min.
Water→50% aqueous acetone in 10 min.
50% 60% aqueous acetone in 40 min.
60% 70% aqueous acetone in 80 min.
Hold at 70% aqueous acetone.

Fraction Collection: 7.25 ml each; HPLC assays and dry residue assays on each.
Results: HPLC data and purity of B1a are shown in Table IV. In composite sample 19–28, 89% of the feed was 27.2% pure B1a. Also a 2.75 fold volume reduction was obtained.

TABLE IV

| Sample | Conc. (mg/ml) | Total (mg) | Recovery % | Solids (mg/ml) | Purity % |
|---|---|---|---|---|---|
| Feed | 0.455 | 91.0 | 100 | 5.15 | 8.84 |
| 1-12. | 0.00 | 0.00 | 0.00 | n.a. | n.a. |
| 13. | trace | trace | trace | n.a. | n.a. |
| 14. | 0.004 | 0.03 | 0.03 | n.a. | n.a. |
| 15. | 0.022 | 0.16 | 0.17 | n.a. | n.a. |
| 16. | 0.119 | 0.86 | 0.95 | 1.64 | 7.26 |
| 17. | 0.289 | 2.10 | 2.30 | 2.50 | 11.56 |
| 18. | 0.533 | 3.86 | 4.25 | 3.53 | 15.10 |
| 19. | 0.943 | 6.84 | 7.51 | 4.40 | 21.43 |
| 20. | 1.39 | 10.07 | 11.07 | 5.20 | 26.71 |
| 21. | 1.55 | 11.23 | 12.34 | 5.57 | 27.81 |
| 22. | 1.48 | 10.73 | 11.79 | 5.03 | 29.42 |
| 23. | 1.39 | 10.05 | 11.04 | 4.51 | 30.73 |
| 24. | 1.27 | 9.19 | 10.10 | 4.18 | 30.34 |
| 25. | 1.07 | 7.74 | 8.51 | 3.57 | 29.92 |
| 26. | 0.866 | 6.28 | 6.90 | 3.24 | 26.73 |
| 27. | 0.691 | 5.01 | 5.51 | 2.71 | 25.50 |
| 28. | 0.520 | 3.77 | 4.14 | 2.65 | 19.62 |
| 29. | 0.373 | 2.70 | 2.97 | 2.41 | 15.48 |
| 30. | 0.272 | 1.97 | 2.17 | 2.17 | 12.54 |
| 31. | 0.195 | 1.41 | 1.55 | 1.93 | 10.10 |
| 32. | 0.141 | 1.02 | 1.12 | 1.81 | 7.79 |
| 33. | 0.093 | 0.68 | 0.74 | 1.60 | 5.84 |
| TOTAL: | | 96.9 | 106.5 | | | n.a. = not assayed

EXAMPLE 5

Use of Duolite® ES-863 Resin

The procedure of Example 4 was repeated except that only 100 ml was fed to the column and the initial water eluant of the gradient elution was omitted.
The results are depicted in Table V.

TABLE V

| Sample | | Conc. (mg/ml) B1a | Conc. (mg/ml) B1b | Total (mg) | Recovery (%) | Solids (mg/ml) | Purity (B1a & B1b) (%) |
|---|---|---|---|---|---|---|---|
| Feed | | 0.447 | 0.071 | 51.8 | 100 | 5.64 | 9.18 |
| El. | 19. | 0.257 | 0.098 | 2.57 | 4.97 | 1.97 | 18.02 |
| | 20. | 0.532 | 0.154 | 4.97 | 9.60 | 2.26 | 30.35 |
| | 21. | 0.796 | 0.177 | 7.05 | 13.62 | 2.44 | 39.88 |
| | 22. | 0.959 | 0.169 | 8.18 | 15.79 | 2.51 | 44.94 |
| | 23. | 1.002 | 0.145 | 8.32 | 16.05 | 2.51 | 45.70 |
| | 24. | 0.868 | 0.111 | 7.10 | 13.70 | 2.33 | 42.02 |
| | 25. | 0.742 | 0.097 | 6.08 | 11.74 | 1.85 | 45.35 |
| | 26. | 0.603 | 0.072 | 4.89 | 9.45 | 1.62 | 41.67 |
| | 27. | 0.454 | 0.055 | 3.69 | 7.12 | 1.48 | 34.39 |
| | 28. | 0.330 | 0.038 | 2.67 | 5.15 | 1.24 | 29.68 |
| | 29. | 0.228 | 0.028 | 1.86 | 3.58 | 1.09 | 23.49 |
| | 30. | 0.150 | 0.019 | 1.23 | 2.37 | 1.04 | 16.25 |
| | 31. | 0.098 | 0.014 | 0.81 | 1.57 | | |
| Overall Recovery: | | | | 59.4 | 115 | | |

EXAMPLE 6

Resin Treatment of Whole Broth Extract

Whole broth (300 ml) was treated with 300 ml of acetone and the mixture was stirred for one hour and filtered. The filtrate (570 ml) was treated as in Example 5 with the same resin column, flow rate, gradient elution, and fraction size. The extraction was 85% efficient and resulted in a concentration of 5 fold relative to whole broth. Fractions 17–24 were combined. The results are shown in Table VI.

TABLE VI

| Sample | | Conc. (mg/ml) B1a | B1b | Total (mg) | Recovery (%) | Solids (mg/ml) | Purity (B1a & B1b) (%) | Volume (ml) |
|---|---|---|---|---|---|---|---|---|
| Feed | | 112 | 10.5 | 69.85 | 100 | 5.60 | 2.19 | 570 |
| El. | 12. | 1.5 | 9.4 | 0.08 | 0.1 | 0.76 | 1.43 | 7.25 |
| | 13. | 6.2 | 57.8 | 0.46 | 0.7 | 0.97 | 6.60 | 7.25 |
| | 14. | 41.3 | 34.7 | 0.55 | 0.8 | 1.24 | 6.13 | 7.25 |
| | 15. | 95.4 | 60.8 | 1.13 | 1.6 | 1.45 | 10.8 | 7.25 |
| | 16. | 205 | 72.9 | 2.01 | 2.8 | 1.88 | 14.8 | 7.25 |
| | 17. | 520 | 125 | 4.68 | 6.8 | 2.36 | 27.3 | 7.25 |
| | 18. | 983 | 170 | 8.36 | 12.0 | 3.16 | 36.5 | 7.25 |
| | 19. | 1315 | 177 | 10.8 | 15.4 | 3.73 | 40.0 | 7.25 |
| | 20. | 1356 | 148 | 10.9 | 15.6 | 3.76 | 40.0 | 7.25 |
| | 21. | 1146 | 114 | 9.14 | 13.1 | 3.41 | 37.0 | 7.25 |
| | 22. | 945 | 86.8 | 7.48 | 10.7 | 2.99 | 34.5 | 7.25 |
| | 23. | 715 | 62.4 | 5.64 | 8.1 | 2.63 | 29.6 | 7.25 |
| | 24. | 515 | 45.0 | 4.06 | 5.8 | 2.27 | 24.7 | 7.25 |
| | 25. | 359 | 34.8 | 2.86 | 4.1 | 1.98 | 19.9 | 7.25 |
| | 26. | 237 | 23.5 | 1.89 | 2.7 | 1.79 | 14.6 | 7.25 |
| | 27. | 162 | 18.5 | 1.31 | 1.9 | 1.71 | 10.6 | 7.25 |
| | 28. | 94.6 | 11.5 | 0.77 | 1.1 | 1.39 | 7.63 | 7.25 |
| | 29. | 54.9 | 6.4 | 0.44 | 0.6 | 1.20 | 5.11 | 7.25 |
| | 30. | 40.6 | 5.5 | 0.33 | 0.5 | 1.25 | 3.69 | 7.25 |
| | 31. | 20.3 | n.d.* | 1.12 | 1.6 | 6.13 | 0.33 | 55 |
| Overall Recovery: | | | | 73.1 | 104.6 | | | |
| Comp. | 17–24 | 1053 | | 61.1 | 87.4 | 3.04 | 34.6 | 58 |

*not detectable

What is claimed is:

1. A process for isolating or separating avermectin compounds from the aqueous fermentation broth that produced such compounds, which comprises:

preparing a mycelial extract by adding acetone to the fermentation broth to from 40 to 60% by volume of the original broth to form a mycelial extract:

treating the aqueous-acetone mycelial extract with an insoluble synthetic resin which is an addition copolymer having a cross linked structure to selectively absorb the avermectin compounds into the resin: and eluting the resin with an aqueous acetone mixture in excess of 60% acetone to remove the avermectin compounds from the resin.

* * * * *